(12) United States Patent
Roessler et al.

(10) Patent No.: US 8,033,160 B2
(45) Date of Patent: Oct. 11, 2011

(54) SENSOR ELEMENT FOR DETERMINING DIFFERENT GAS COMPONENTS IN A TEST GAS

(75) Inventors: Mario Roessler, Ceske Budejovice (CZ); Bernd Schumann, Rutesheim (DE); Berndt Cramer, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 422 days.

(21) Appl. No.: 12/086,326

(22) PCT Filed: Nov. 16, 2006

(86) PCT No.: PCT/EP2006/068556
§ 371 (c)(1),
(2), (4) Date: Mar. 9, 2009

(87) PCT Pub. No.: WO2007/068548
PCT Pub. Date: Jun. 21, 2007

(65) Prior Publication Data
US 2009/0223204 A1    Sep. 10, 2009

(30) Foreign Application Priority Data
Dec. 13, 2005  (DE) .......................... 10 2005 059 434

(51) Int. Cl.
*G01N 27/26* (2006.01)
(52) U.S. Cl. ...................................... 73/31.06; 204/424

(58) Field of Classification Search .................. 204/424, 204/425, 426; 73/31.06
See application file for complete search history.

(56) References Cited

U.S. PATENT DOCUMENTS 6,451,187 B1 * 9/2002 Suzuki et al. ................. 204/426
2006/0108220 A1 * 5/2006 Betsill .......................... 204/412

FOREIGN PATENT DOCUMENTS

| EP | 0706048 | 4/1996 |
| EP | 0750192 | 12/1996 |
| WO | WO 96/26434 | 8/1996 |

OTHER PUBLICATIONS

Scalwig et al., "Gas sensitive GaN/AlGaN-heterostructures", Sensors and Actuators B, 202, vol. 87, pp. 425-530.*
International Search Report, PCT International Patent Application No. PCT/EP2006/068556, dated Mar. 8, 2007.

* cited by examiner

*Primary Examiner* — Lisa Caputo
*Assistant Examiner* — Punam Roy
(74) *Attorney, Agent, or Firm* — Kenyon & Kenyon LLP

(57) ABSTRACT

A sensor element for determining different gas components in a test gas, in particular in an exhaust gas of an internal combustion engine, including a lambda sensor for determining an oxygen content in the test gas, at least one semiconductor gas sensor for determining at least one further gas component in the test gas, and a multiplexer which is connected to the semiconductor gas sensor.

11 Claims, 1 Drawing Sheet

SENSOR ELEMENT FOR DETERMINING DIFFERENT GAS COMPONENTS IN A TEST GAS

BACKGROUND INFORMATION

The present invention relates to a sensor element for determining different gas components in a test gas, in particular in an exhaust gas of an internal combustion engine.

FIELD OF THE INVENTION

Sensor elements for determining gas components in a test gas are available in different embodiments. In the automobile industry, for example, lambda sensors are used to measure the oxygen content in the exhaust gas in order to regulate the combustion process on the basis of the measurement result. Sensor elements of this type are situated in the hot exhaust gas stream and are exposed to very high temperatures. Modern sensor elements are designed as electrochemical solid electrolyte sensors and have a heater for heating the sensor element to temperatures of approximately 750° C. To make further improvement in the efficiency of the internal combustion engine and reduction of exhaust gases possible, often it is, however, necessary to ascertain further gas components in the exhaust gas in addition to the oxygen content.

SUMMARY

An example sensor element according to the present invention may have the advantage that it is able to determine different gas components in a test gas, in particular in an exhaust gas of an internal combustion engine. Only a single sensor element is needed therefor. The sensor element includes, on the one hand, a lambda sensor for determining the oxygen component in the test gas and at least one semiconductor gas sensor for determining at least one further gas component in the test gas. Furthermore, the sensor element includes a multiplexer, which is connected to the semiconductor gas sensor. The use of the multiplexer makes local signal processing possible, thus significantly reducing the sensitivity of the sensor element to interference. The multiplexer makes it possible to save signal lines because it has preferably only one output for a plurality of inputs. The multiplexer thus reduces the number of sensor terminals of the sensor element. This makes a particularly cost-effective manufacture of the sensor element possible.

The example semiconductor gas sensor is preferably designed as a multigas sensor and has at least one gas-sensitive gate on a semiconductor module for each gas component to be determined in the test gas. As an alternative, a plurality of separate semiconductor gas sensors may also be provided, each of which is able to determine only one gas component in the test gas. A system of this type, however, needs a relatively large installation space, so that the design of the semiconductor gas sensor as a multigas sensor is preferred from the manufacturing point of view and because of its compactness.

According to another preferred example embodiment of the present invention, the multiplexer is integrated in the semiconductor gas sensor. This allows a particularly compact design to be implemented and, in particular, separate connecting lines between the semiconductor gas sensor and the multiplexer may be omitted.

According to another preferred exemplary embodiment of the present invention, the multiplexer and the semiconductor gas sensor are separate components. This allows the use of standard components for the multiplexer, for example.

A clock pulse to be predefined for operating the multiplexer for switching over the measuring signals at the inputs to the output(s) is preferably generated by a clock pulse-generating circuit situated in the multiplexer.

According to an alternative example embodiment of the present invention, a clock pulse to be predefined for the multiplexer is generated by an external clock pulse-generating device. The external clock pulse-generating device is preferably a clock pulse-generating device for a heating device of the sensor element in particular. This clock pulse-generating device is, for example, a pulse-width modulation of the heating device of the sensor element which is heated in a periodically clocked manner with the aid of the heating device. This requires only one connection of the multiplexer to the clock pulse-generating device of the heating device to be provided. This allows the multiplexer to be designed to be simple and compact in particular and the sensor element to be manufactured very cost-effectively. Furthermore, synchronization of the measurement of the data exchange and the heating is then preferably possible to minimize interfering mutual signal influences.

Furthermore, the example semiconductor gas sensor is preferably manufactured using high-temperature semiconductors such as SiC, GaN, or GaAlN. This results in no material-related problems with the semiconductor gas sensor even at high exhaust gas temperatures over 300° C.

A monoflop circuit is preferably situated between the external clock pulse-generating device for the multiplexer and the multiplexer. This allows a delay to be set between the multiplexer switchover and the clock pulses. This is advantageous in particular when the external clock pulse-generating device for the heating device of the sensor element is used for the multiplexer, where there is the risk that the current or the voltage for the heating device is injected into the sensor signals.

The example sensor element according to the present invention is used particularly advantageously in vehicles for determining different gas components in the exhaust gas of the vehicle. Oxygen and/or nitrogen oxides and/or carbon monoxide and/or ammonia and/or hydrocarbons, etc. are preferably determined as gases in the exhaust gas.

BRIEF DESCRIPTION OF THE DRAWINGS

The present invention is described below with reference to preferred exemplary embodiments in connection with the figures.

DETAILED DESCRIPTION OF EXAMPLE EMBODIMENTS

A sensor element 1 according to a first exemplary embodiment of the present invention is described below with reference to FIGS. 1 and 2.

Figure 1:
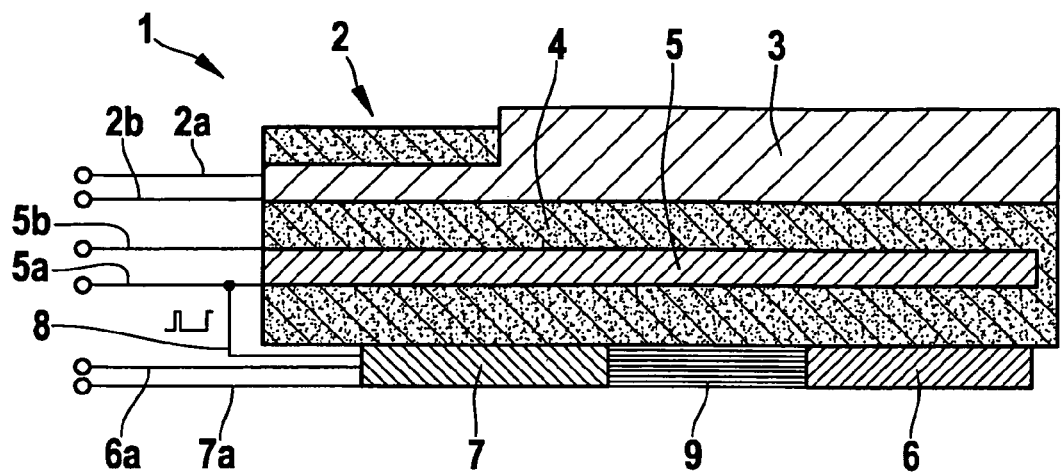
FIG. 1 shows a schematic sectional view of a sensor element according to a first exemplary embodiment of the present invention.
Figure 2:
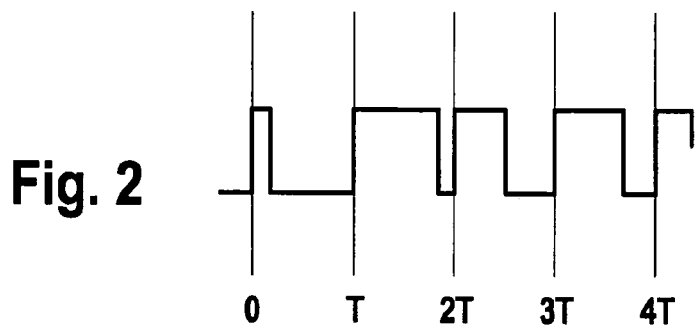
FIG. 2 shows a schematic depiction of a clock pulse sequence of a pulse-width modulation for a heating device of the sensor element.

As FIG. 1 shows, sensor element 1 includes a lambda sensor 2 for determining the oxygen content in the exhaust gas of an internal combustion engine. Lambda sensor 2 has a conventional design and is depicted only schematically in FIG. 1. Lambda sensor 2 includes a sensor unit 3, which is situated on a base material 4, in particular a solid electrolyte such as, for example, zirconium oxide. Furthermore, lambda sensor 2 includes a heating device 5. In FIG. 1, terminals 2a, 2b are also shown for lambda sensor 2. Depending on the type of the lambda sensor, more terminals may also be provided. Heating device 5 also includes two terminals 5a, 5b, heating device 5 being heated with the aid of a pulse-width modulation method or a method clocked using a fixed period. Heating device 5 ensures that the lambda sensor has the necessary temperature of approximately 750° C. during operation. This may be achieved, for example, by measuring the internal resistance of terminals 2a and 2b.

Sensor element 1 according to the example embodiment of the present invention furthermore includes a semiconductor gas sensor 6 which is situated on lambda sensor 2. Semiconductor gas sensor 6 includes a plurality of sensor units to determine other different gas components in the exhaust gas. The sensor units are manufactured of high-temperature semiconductors such as, for example, SiC, GaN or GaAlN. Semiconductor gas sensor 6 is also situated in the exhaust gas stream. A semiconductor component such as, for example, a field-effect transistor which is sensitive to a predetermined gas or a certain group of gases, is thus situated on semiconductor gas sensor 6 for each gas type of the test gas to be determined. Each of these sensor units on semiconductor gas sensor 6 delivers at least one electrical signal which is used for determining the gas concentration to be measured.

As FIG. 1 shows, example sensor element 1 furthermore includes a multiplexer 7, which is also situated on lambda sensor 2. Multiplexer 7 is an electrical circuit which switches the signals of a plurality of sensor units coming from semiconductor gas sensor 6 sequentially in a predefined cycle to one or more output channels. In the exemplary embodiment described, multiplexer 7 has a single output 7a. As FIG. 1 shows, multiplexer 7 is connected to semiconductor gas sensor 6, more precisely to the individual sensor units of the semiconductor gas sensor, via a plurality of connecting lines 9. A feed line to semiconductor gas sensor 6 is labeled with reference numeral 6a in FIG. 1.

As FIG. 1 shows, sensor element 1 has a very compact overall design. Multiplexer 7 and semiconductor gas sensor 6 are situated on an outside of lambda sensor 2.

Furthermore, a connecting line 8 is provided between a terminal 5a of heating device 5 and multiplexer 7. A clock signal used for operating heating device 5 is transmitted to multiplexer 7 via connecting line 8. FIG. 2 schematically shows one possible design of the clock signal in the form of a pulse-width modulation. The clock signal has a fixed basic clock pulse; the successive pulses do not overlap. This clock pulse T for heating device 5 is thus also used as a clock pulse for multiplexer 7. An external clock pulse for converting the parallel signals supplied to the multiplexer into serial signals for output 7a of multiplexer 7 is thus predefined for multiplexer 7. Output 7a of the multiplexer is connected to an analyzer circuit (not depicted). Multiplexer thus makes it possible to reduce the number of terminals of the sensor element. Since multiplexer 7 is used as the clock pulse of heating device 5, a particularly simple design results. If pulse-width modulation is used as the clock pulse for operating heating device 5, however, attention is paid so that the maximum pulse width is not as large as the base clock pulse, i.e., that two successive pulses are still separated in time. This may be achieved, for example, by a pause of a few microseconds to milliseconds to be inserted. It is particularly advantageous if the multiplexer is operated in such a way that, for example, it responds to the rising edge of clock pulse T for the heating device. It is to be furthermore noted that basically a non-periodic signal may also be used as the timer for multiplexer 7.

Lambda sensor 2 may be any type of lambda sensor. The lambda sensor may be a discrete-level sensor or a purely amperometric limit current sensor without a reference electrode or a pump sensor or an amperometric limit current sensor having a reference electrode or a broadband sensor. In all lambda sensors that may be used, only two further terminals 6a, 7a are provided due to the additional function of sensor element 1 according to the present invention for determining further gas types. It is to be pointed out that multiplexer 7 may also be designed, as an alternative, in such a way that it has more than a single output 7a.

It may be advantageous to situate a monoflop circuit between multiplexer 7 and line 8 because the heater current and the heater voltage for heating device 5 may be injected into the sensor signals. Furthermore, the monoflop circuit makes it possible to frequency divide the switchover pulses if the clock signal upstream or downstream from the multiplexer is to be additionally integrated. This allows the accuracy to be enhanced for a longer period of time.

Figure 3:
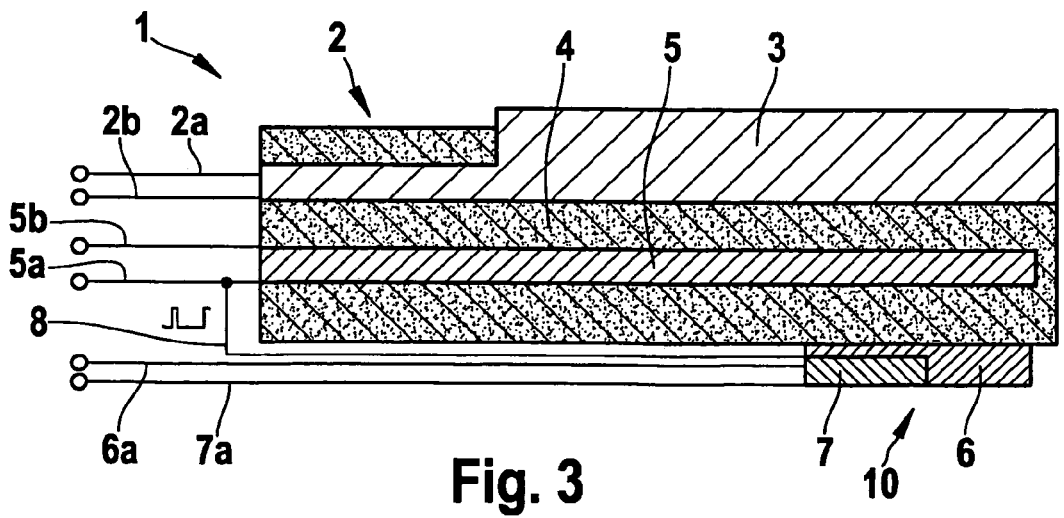
FIG. 3 shows a schematic sectional view of a sensor element according to a second exemplary embodiment of the present invention.

An example sensor element 1 according to a second exemplary embodiment of the present invention is described below with reference to FIG. 3. Identical or functionally identical components are labeled with the same reference numerals as in the first exemplary embodiment of the present invention.

Unlike the first exemplary embodiment, sensor element 1 of the second exemplary embodiment includes an integrated component 10, which includes semiconductor gas sensor 6 and multiplexer 7. In other words, multiplexer 7 is integrated in semiconductor gas sensor 6, so that an integrated component 10 is provided. This allows the plurality of connecting lines 9 between semiconductor gas sensor 6 and multiplexer 7 to be omitted. Sensor element 7 may thus be designed to be even more compact and to be manufactured more cost-effectively. Otherwise this exemplary embodiment corresponds to the previous exemplary embodiment, so that reference may be made to the description given therein.

What claimed is:

1. A sensor element for determining different gas components in a test gas, comprising:
   a lambda sensor to determine an oxygen content in the test gas;
   at least one semiconductor gas sensor to determine at least one further gas component in the test gas;
   a multiplexer connected to the semiconductor gas sensor; and
   an external clock pulse-generating device to provide a clock pulse for the multiplexer,
   wherein an external clock pulse-generating device to operate a heating device of the lambda sensor is connected to the multiplexer via a line.

2. The sensor element as recited in claim 1, wherein the test gas is an exhaust gas of an internal combustion engine.

3. The sensor element as recited in claim 1, wherein the semiconductor gas sensor is a multigas sensor to determine a plurality of different gas component, the semiconductor gas sensor having at least one semiconductor component for each gas component to be determined.

4. The sensor element as recited in claim 1, wherein the multiplexer is integrated in the semiconductor gas sensor to provide an integrated component.

5. The sensor element as recited in claim 1, wherein the multiplexer is situated separately from the semiconductor gas sensor on the lambda sensor.

6. The sensor element as recited in claim 1, wherein the multiplexer includes a separate circuit integrated in the multiplexer, the separate circuit generating a clock pulse of the multiplexer.

7. The sensor element as recited in claim 1, wherein the external clock pulse-generating device is a pulse-width modulation.

8. The sensor element as recited in claim 1, wherein a monoflop circuit is situated between the external clock pulse-generating device and the multiplexer.

9. The sensor element as recited in claim 1, wherein the semiconductor gas sensor includes sensor units made of a high-temperature semiconductor.

10. The sensor element as recited in claim 9, wherein the high-temperature semiconductor is one of GaN, SiC, or GaAlN.

11. A vehicle, comprising:
an internal combustion engine which has an exhaust gas; and
a sensor element to determine different gas components in the exhaust gas, the sensor element including a lambda sensor to determine an oxygen content in the exhaust gas, at least one semiconductor gas sensor to determine at least one further gas component in the exhaust gas, a multiplexer connected to the semiconductor gas sensor, and an external clock pulse-generating device to provide a clock pulse for the multiplexer, wherein an external clock pulse-generating device to operate a heating device of the lambda sensor is connected to the multiplexer via a line.

* * * * *